(12) United States Patent
Carleo (10) Patent No.: US 10,149,961 B2
(45) Date of Patent: Dec. 11, 2018

(54) CATHETER HAVING IMPROVED DRAINAGE AND/OR A RETRACTABLE SLEEVE AND METHOD OF USING THE SAME

(75) Inventor: Steven Carleo, Covington, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 556 days.

(21) Appl. No.: 13/387,447

(22) PCT Filed: Aug. 28, 2009

(86) PCT No.: PCT/US2009/055395
§ 371 (c)(1),
(2), (4) Date: Mar. 22, 2012

(87) PCT Pub. No.: WO2011/014201
PCT Pub. Date: Feb. 3, 2011

(65) Prior Publication Data
US 2012/0179144 A1  Jul. 12, 2012

Related U.S. Application Data

(60) Provisional application No. 61/229,563, filed on Jul. 29, 2009.

(51) Int. Cl.
*A61M 27/00* (2006.01)
*A61M 25/00* (2006.01)
(Continued)

(52) U.S. Cl.
CPC ...... *A61M 25/0017* (2013.01); *A61M 25/007* (2013.01); *A61M 25/0111* (2013.01);
(Continued)

(58) Field of Classification Search
CPC .. A61M 2025/0687; A61M 2025/1081; A61M 2039/1066; A61M 5/3243;
(Continued)

(56) References Cited

U.S. PATENT DOCUMENTS 1,888,349 A   11/1932  Jacoby
2,912,981 A   11/1959  Keough
(Continued)

FOREIGN PATENT DOCUMENTS

CA   2770300 A1   2/2011
CA   2769026 C    4/2015
(Continued)

OTHER PUBLICATIONS

Kramann, Bernhard, Catheter with Insertion Aid, Translation of EP0247559B1.*

(Continued)

*Primary Examiner* — Kai Weng
(74) *Attorney, Agent, or Firm* — Rutan & Tucker, LLP (57) ABSTRACT

A catheter includes an elongate member (12) having a proximal end and a distal end. The distal end has at least one drainage opening (20). At least one of; the at least one drainage opening (20) is a single elongate opening, or is two circumferentially spaced elongate openings (FIG. 5), or is at least three staggered openings (FIG. 3), or is an array of staggered openings (FIG. 3). Alternatively or additionally, a sleeve member (10) is arranged on the elongate member (12) and is movable at least between a first position (FIG. 1) covering the at least one drainage opening (20) and a second position (FIG. 2) which allows fluid to pass into the catheter. A method of using the catheter includes inserting a catheter having a retractable sleeve (10) into a user's body and retracting the retractable sleeve (10) to expose drainage openings (20) and drain fluid from the body.

17 Claims, 3 Drawing Sheets (51) Int. Cl.
  *A61M 25/01* (2006.01)
  *A61M 25/06* (2006.01)
(52) U.S. Cl.
  CPC ... *A61M 25/002* (2013.01); *A61M 2025/0046* (2013.01); *A61M 2025/0056* (2013.01); *A61M 2025/0681* (2013.01)
(58) Field of Classification Search
  CPC .............. A61M 5/3257; A61M 5/3271; A61M 25/0026; A61M 2025/0034; A61M 2025/0175; A61M 2025/0681
  USPC .............. 604/93.01, 171–172, 317–321, 544
  See application file for complete search history.

(56) References Cited

U.S. PATENT DOCUMENTS

| | | |
|---|---|---|
| 2,919,697 A | 1/1960 | Kim |
| 3,173,566 A | 3/1965 | Talbert |
| 3,344,791 A | 10/1967 | Foderick |
| 3,556,294 A | 1/1971 | Walck et al. |
| 3,556,874 A | 1/1971 | McClain |
| 3,566,874 A | 3/1971 | Shepherd et al. |
| 3,648,704 A | 3/1972 | Jackson |
| 3,695,921 A | 10/1972 | Shepard et al. |
| 3,699,964 A | 10/1972 | Ericson |
| 3,726,281 A | 4/1973 | Norton et al. |
| 3,794,042 A | 2/1974 | De Klotz et al. |
| 3,802,987 A | 4/1974 | Noll |
| 3,835,992 A | 9/1974 | Adams, IV |
| 3,854,483 A | 12/1974 | Powers |
| 3,861,395 A | 1/1975 | Taniguchi |
| 3,894,540 A | 7/1975 | Bonner, Jr. |
| 3,898,993 A | 8/1975 | Taniguchi |
| 3,934,721 A | 1/1976 | Juster et al. |
| 3,967,728 A | 7/1976 | Gordon et al. |
| 4,026,296 A | 5/1977 | Stoy et al. |
| 4,051,849 A | 10/1977 | Poncy et al. |
| 4,055,682 A | 10/1977 | Merrill |
| 4,062,363 A | 12/1977 | Bonner, Jr. |
| 4,069,359 A | 1/1978 | DeMarse et al. |
| 4,091,922 A | 5/1978 | Egler |
| 4,140,127 A | 2/1979 | Cianci et al. |
| 4,198,983 A | 4/1980 | Becker et al. |
| 4,230,115 A | 10/1980 | Walz, Jr. et al. |
| 4,245,639 A | 1/1981 | La Rosa |
| 4,246,909 A | 1/1981 | Wu et al. |
| 4,269,310 A | 5/1981 | Uson et al. |
| 4,306,557 A | 12/1981 | North |
| 4,350,161 A | 9/1982 | Davis, Jr. |
| 4,351,333 A | 9/1982 | Lazarus et al. |
| 4,366,901 A | 1/1983 | Short |
| 4,392,848 A | 7/1983 | Lucas et al. |
| 4,411,648 A | 10/1983 | Davis et al. |
| 4,515,593 A | 5/1985 | Norton |
| 4,517,971 A | 5/1985 | Sorbonne |
| 4,560,382 A | 12/1985 | Isono et al. |
| 4,571,241 A | 2/1986 | Christopher |
| 4,585,666 A | 4/1986 | Lambert |
| 4,597,765 A | 7/1986 | Klatt |
| 4,607,746 A | 8/1986 | Stinnette |
| 4,610,670 A | 9/1986 | Spencer |
| 4,619,642 A | 10/1986 | Spencer |
| 4,681,572 A | 7/1987 | Tokarz et al. |
| 4,692,154 A | 9/1987 | Singery et al. |
| 4,696,672 A | 9/1987 | Mochizuki et al. |
| 4,704,102 A | 11/1987 | Guthery |
| 4,723,946 A | 2/1988 | Kay |
| 4,738,667 A | 4/1988 | Galloway |
| 4,754,877 A | 7/1988 | Johansson et al. |
| 4,759,753 A | 7/1988 | Schneider et al. |
| 4,762,128 A | 8/1988 | Rosenbluth |
| 4,773,901 A | 9/1988 | Norton |
| 4,784,651 A | 11/1988 | Hickey et al. |
| 4,811,847 A | 3/1989 | Reif et al. |
| 4,838,876 A | 6/1989 | Wong et al. |
| 4,886,508 A | 12/1989 | Washington |
| 4,888,005 A | 12/1989 | Dingeman et al. |
| 4,893,623 A | 1/1990 | Rosenbluth |
| 4,932,938 A | 6/1990 | Goldberg et al. |
| 4,957,487 A | 9/1990 | Gerow |
| 4,997,426 A | 3/1991 | Dingeman et al. |
| 5,007,897 A | 4/1991 | Kalb et al. |
| 5,045,078 A | 9/1991 | Asta |
| 5,077,352 A | 12/1991 | Elton |
| 5,087,252 A | 2/1992 | Denard |
| 5,098,379 A | 3/1992 | Conway et al. |
| 5,100,396 A | 3/1992 | Zamierowski |
| 5,137,671 A | 8/1992 | Conway et al. |
| 5,147,341 A | 9/1992 | Starke et al. |
| 5,174,290 A | 12/1992 | Fiddian-Green |
| 5,179,174 A | 1/1993 | Elton |
| 5,180,591 A | 1/1993 | Magruder et al. |
| 5,186,172 A | 2/1993 | Fiddian-Green |
| 5,188,596 A | 2/1993 | Condon et al. |
| 5,201,724 A | 4/1993 | Hukins et al. |
| 5,209,726 A | 5/1993 | Goosen |
| 5,209,728 A | 5/1993 | Kraus et al. |
| 5,224,953 A | 7/1993 | Morgentaler |
| 5,226,530 A | 7/1993 | Golden |
| 5,234,411 A | 8/1993 | Vaillancourt |
| 5,236,422 A | 8/1993 | Eplett, Jr. |
| 5,242,398 A | 9/1993 | Knoll et al. |
| 5,242,428 A | 9/1993 | Palestrant |
| 5,261,896 A | 11/1993 | Conway et al. |
| 5,269,755 A | 12/1993 | Bodicky |
| 5,269,770 A | 12/1993 | Conway et al. |
| 5,282,795 A | 2/1994 | Finney |
| 5,352,182 A | 10/1994 | Kalb et al. |
| 5,360,402 A | 11/1994 | Conway et al. |
| 5,370,899 A | 12/1994 | Conway et al. |
| 5,415,165 A | 5/1995 | Fiddian-Green |
| 5,417,666 A | 5/1995 | Coulter |
| 5,433,713 A | 7/1995 | Trotta |
| 5,445,626 A | 8/1995 | Gigante et al. |
| 5,447,231 A | 9/1995 | Kastenhofer |
| 5,454,798 A | 10/1995 | Kubalak et al. |
| 5,456,251 A | 10/1995 | Fiddian-Green |
| 5,466,229 A | 11/1995 | Elson et al. |
| 5,476,434 A | 12/1995 | Kalb et al. |
| 5,482,740 A | 1/1996 | Conway et al. |
| 5,501,669 A | 3/1996 | Conway et al. |
| 5,509,889 A | 4/1996 | Kalb et al. |
| 5,514,112 A | 5/1996 | Chu et al. |
| 5,520,636 A | 5/1996 | Korth et al. |
| 5,531,715 A | 7/1996 | Engelson et al. |
| 5,531,717 A | 7/1996 | Roberto et al. |
| 5,536,258 A | 7/1996 | Folden |
| 5,558,900 A | 9/1996 | Fan et al. |
| 5,569,219 A | 10/1996 | Hakki et al. |
| 5,582,599 A | 12/1996 | Daneshvar |
| 5,591,292 A | 1/1997 | Blomqvist |
| 5,599,321 A | 2/1997 | Conway et al. |
| 5,601,537 A | 2/1997 | Frassica |
| 5,607,417 A | 3/1997 | Batich et al. |
| 5,616,126 A | 4/1997 | Malekmehr et al. |
| 5,624,395 A | 4/1997 | Mikhail et al. |
| 5,653,700 A | 8/1997 | Byrne et al. |
| 5,670,111 A | 9/1997 | Conway et al. |
| 5,688,516 A | 11/1997 | Raad et al. |
| 5,704,353 A | 1/1998 | Kalb et al. |
| 5,707,357 A | 1/1998 | Mikhail et al. |
| 5,711,841 A | 1/1998 | Jaker |
| 5,749,826 A | 5/1998 | Faulkner |
| 5,779,670 A | 7/1998 | Bidwell et al. |
| 5,782,808 A | 7/1998 | Folden |
| 5,785,694 A | 7/1998 | Cohen et al. |
| 5,788,687 A | 8/1998 | Batich et al. |
| 5,800,339 A | 9/1998 | Salama |
| 5,817,067 A | 10/1998 | Tsukada et al. |
| 5,820,583 A | 10/1998 | Demopulos et al. |
| 5,840,151 A | 11/1998 | Munsch |
| 5,848,691 A | 12/1998 | Morris et al. |
| 5,853,518 A | 12/1998 | Utas et al. |

(56) References Cited

U.S. PATENT DOCUMENTS

| | | |
|---|---|---|
| 5,871,475 A | 2/1999 | Frassica |
| 5,895,374 A | 4/1999 | Rodsten et al. |
| 5,897,535 A | 4/1999 | Feliziani et al. |
| 5,941,856 A | 8/1999 | Kovacs et al. |
| 5,971,954 A | 10/1999 | Conway et al. |
| 5,980,483 A | 11/1999 | Dimitri et al. |
| 5,989,230 A | 11/1999 | Frassica |
| 6,004,305 A | 12/1999 | Hursman et al. |
| 6,007,521 A * | 12/1999 | Bidwell et al. ............... 604/264 |
| 6,024,751 A | 2/2000 | Lovato et al. |
| 6,050,934 A | 4/2000 | Mikhail et al. |
| 6,053,905 A | 4/2000 | Daignault, Jr. et al. |
| 6,056,715 A | 5/2000 | Demopulos et al. |
| 6,059,107 A | 5/2000 | Nosted et al. |
| 6,063,063 A | 5/2000 | Harboe et al. |
| 6,090,075 A | 7/2000 | House |
| 6,156,049 A | 12/2000 | Lovato et al. |
| 6,162,201 A | 12/2000 | Cohen et al. |
| 6,183,461 B1 | 2/2001 | Matsuura et al. |
| 6,186,990 B1 | 2/2001 | Chen et al. |
| 6,190,353 B1 | 2/2001 | Makower et al. |
| 6,210,394 B1 | 4/2001 | Demopulos et al. |
| 6,217,569 B1 | 4/2001 | Fiore |
| 6,221,056 B1 | 4/2001 | Silverman |
| 6,238,383 B1 | 5/2001 | Karram et al. |
| 6,254,570 B1 | 7/2001 | Rutner et al. |
| 6,254,582 B1 | 7/2001 | O'Donnell et al. |
| 6,254,585 B1 | 7/2001 | Demopulos et al. |
| 6,261,279 B1 | 7/2001 | Demopulos et al. |
| 6,293,923 B1 | 9/2001 | Yachia et al. |
| 6,299,598 B1 | 10/2001 | Bander |
| 6,306,422 B1 | 10/2001 | Batich et al. |
| 6,329,488 B1 | 12/2001 | Terry et al. |
| 6,340,359 B1 | 1/2002 | Silverman |
| 6,355,004 B1 | 3/2002 | Pedersen et al. |
| 6,358,229 B1 | 3/2002 | Tihon |
| 6,368,315 B1 | 4/2002 | Gillis et al. |
| 6,368,317 B2 | 4/2002 | Chang |
| 6,379,334 B1 | 4/2002 | Frassica |
| 6,383,434 B2 | 5/2002 | Conway et al. |
| 6,391,010 B1 | 5/2002 | Wilcox |
| 6,391,014 B1 | 5/2002 | Silverman |
| 6,398,718 B1 | 6/2002 | Yachia et al. |
| 6,402,726 B1 | 6/2002 | Genese |
| 6,409,717 B1 | 6/2002 | Israelsson et al. |
| 6,458,867 B1 | 10/2002 | Wang et al. |
| 6,468,245 B2 | 10/2002 | Alexandersen et al. |
| 6,485,476 B1 | 11/2002 | von Dyck et al. |
| 6,544,240 B1 | 4/2003 | Borodulin et al. |
| 6,578,709 B1 | 6/2003 | Kavanagh et al. |
| 6,582,401 B1 | 6/2003 | Windheuser et al. |
| 6,602,244 B2 | 8/2003 | Kavanagh et al. |
| 6,613,342 B2 | 9/2003 | Aoki |
| 6,626,888 B1 | 9/2003 | Conway et al. |
| 6,629,969 B2 | 10/2003 | Chan et al. |
| 6,634,498 B2 | 10/2003 | Kayerod et al. |
| 6,638,269 B2 | 10/2003 | Wilcox |
| 6,648,906 B2 | 11/2003 | Lasheras et al. |
| 6,659,937 B2 | 12/2003 | Polsky et al. |
| 6,682,555 B2 | 1/2004 | Cioanta et al. |
| 6,695,831 B1 | 2/2004 | Tsukada et al. |
| 6,711,436 B1 | 3/2004 | Duhaylongsod |
| 6,716,895 B1 | 4/2004 | Terry |
| 6,719,709 B2 | 4/2004 | Whalen et al. |
| 6,730,113 B2 | 5/2004 | Eckhardt et al. |
| 6,736,805 B2 | 5/2004 | Israelsson et al. |
| 6,746,421 B2 | 6/2004 | Yachia et al. |
| 6,783,520 B1 | 8/2004 | Candray et al. |
| D496,266 S | 9/2004 | Nestenborg et al. |
| 6,824,532 B2 | 11/2004 | Gillis et al. |
| 6,835,183 B2 | 12/2004 | Lennox et al. |
| 6,840,379 B2 | 1/2005 | Franks-Farah et al. |
| 6,848,574 B1 | 2/2005 | Israelsson et al. |
| 6,849,070 B1 | 2/2005 | Hansen et al. |
| 6,852,105 B2 | 2/2005 | Bolmsjo et al. |
| D503,335 S | 3/2005 | Risberg et al. |
| 6,869,416 B2 | 3/2005 | Windheuser et al. |
| 6,887,230 B2 | 5/2005 | Kubalak et al. |
| 6,889,740 B1 | 5/2005 | Globensky et al. |
| 6,918,924 B2 | 7/2005 | Lasheras et al. |
| 6,926,708 B1 | 8/2005 | Franks-Farah et al. |
| 6,939,339 B1 | 9/2005 | Axexandersen et al. |
| 6,941,171 B2 | 9/2005 | Mann et al. |
| 6,942,634 B2 | 9/2005 | Odland |
| 6,945,957 B2 | 9/2005 | Freyman |
| 6,949,598 B2 | 9/2005 | Terry |
| 7,001,370 B2 | 2/2006 | Kubalak et al. |
| 7,048,717 B1 | 5/2006 | Frassica |
| 7,059,330 B1 | 6/2006 | Makower et al. |
| 7,066,912 B2 | 6/2006 | Nestenborg et al. |
| 7,087,041 B2 | 8/2006 | von Dyck et al. |
| 7,087,048 B2 | 8/2006 | Israelsson et al. |
| 7,094,220 B2 | 8/2006 | Tanghoj et al. |
| 7,160,277 B2 | 1/2007 | Elson et al. |
| 7,166,092 B2 | 1/2007 | Elson et al. |
| 7,195,608 B2 | 3/2007 | Burnett |
| 7,244,242 B2 | 7/2007 | Freyman |
| 7,250,043 B2 | 7/2007 | Chan et al. |
| 7,255,687 B2 | 8/2007 | Huang et al. |
| 7,270,647 B2 | 9/2007 | Karpowicz et al. |
| 7,294,117 B2 | 11/2007 | Provost-tine et al. |
| 7,311,690 B2 | 12/2007 | Burnett |
| 7,311,698 B2 | 12/2007 | Tanghoj et al. |
| 7,331,948 B2 | 2/2008 | Skarda |
| 7,334,679 B2 | 2/2008 | Givens, Jr. |
| 7,374,040 B2 | 5/2008 | Lee et al. |
| 7,380,658 B2 | 6/2008 | Murray et al. |
| 7,445,812 B2 | 11/2008 | Schmidt et al. |
| 7,458,964 B2 | 12/2008 | Mosler et al. |
| 7,476,223 B2 | 1/2009 | McBride |
| 7,507,229 B2 | 3/2009 | Hewitt et al. |
| 7,517,343 B2 | 4/2009 | Tanghoj et al. |
| 7,537,589 B2 | 5/2009 | Tsukada et al. |
| 7,571,804 B2 | 8/2009 | Kjellmann Bruun et al. |
| 7,601,158 B2 | 10/2009 | House |
| 7,615,045 B2 | 11/2009 | Israelsson et al. |
| 7,628,784 B2 | 12/2009 | Diaz et al. |
| 7,632,256 B2 | 12/2009 | Mosler et al. |
| 7,662,146 B2 | 2/2010 | House |
| 7,682,353 B2 | 3/2010 | Tanghoj et al. |
| 7,770,726 B2 | 8/2010 | Murray et al. |
| 7,789,873 B2 | 9/2010 | Kubalak et al. |
| 7,823,722 B2 | 11/2010 | Bezou et al. |
| 7,846,133 B2 | 12/2010 | Windheuser et al. |
| 7,938,838 B2 | 5/2011 | House |
| 7,947,021 B2 | 5/2011 | Bourne et al. |
| 7,985,217 B2 | 7/2011 | Mosler et al. |
| 8,011,505 B2 | 9/2011 | Murray et al. |
| 8,051,981 B2 | 11/2011 | Murray et al. |
| 8,066,693 B2 | 11/2011 | Tanghoj et al. |
| 8,177,774 B2 | 5/2012 | House |
| 8,181,778 B1 | 5/2012 | Van Groningen et al. |
| 8,205,745 B2 | 6/2012 | Murray et al. |
| 8,328,792 B2 | 12/2012 | Nishtala et al. |
| 8,454,569 B2 | 6/2013 | Kull-Osterlin et al. |
| 8,459,455 B2 | 6/2013 | Frojd |
| 8,475,434 B2 | 7/2013 | Frojd |
| 8,998,882 B2 | 4/2015 | Knapp et al. |
| 9,033,149 B2 | 5/2015 | Terry |
| 9,114,227 B2 | 8/2015 | Blanchard |
| 9,694,113 B2 | 7/2017 | Knapp et al. |
| 9,731,093 B2 | 8/2017 | Terry |
| 9,821,139 B2 | 11/2017 | Carleo |
| 2001/0001443 A1 | 5/2001 | Kayerod et al. |
| 2001/0031952 A1 | 10/2001 | Karram et al. |
| 2001/0047147 A1 | 11/2001 | Slepian et al. |
| 2001/0054562 A1 | 12/2001 | Pettersson et al. |
| 2002/0007175 A1 | 1/2002 | Chang |
| 2002/0045855 A1 | 4/2002 | Frassica |
| 2002/0055730 A1 | 5/2002 | Yachia et al. |
| 2002/0077611 A1 | 6/2002 | von Dyck et al. |
| 2002/0082551 A1 | 6/2002 | Yachia et al. |
| 2002/0087131 A1 | 7/2002 | Wolff et al. |
| 2002/0094322 A1 | 7/2002 | Lawson et al. |

(56) References Cited

U.S. PATENT DOCUMENTS

| | | |
|---|---|---|
| 2002/0095133 A1 | 7/2002 | Gillis et al. |
| 2002/0099356 A1 | 7/2002 | Unger et al. |
| 2002/0103467 A1 | 8/2002 | Kubalak |
| 2002/0107467 A1 | 8/2002 | Levin |
| 2002/0132013 A1 | 9/2002 | Moulis |
| 2002/0133130 A1 | 9/2002 | Wilcox |
| 2002/0156440 A1 | 10/2002 | Israelsson et al. |
| 2002/0165427 A1 | 11/2002 | Yachia et al. |
| 2003/0004496 A1 | 1/2003 | Tanghoj |
| 2003/0018293 A1 | 1/2003 | Tanghoj et al. |
| 2003/0018302 A1 | 1/2003 | Kavanagh et al. |
| 2003/0018322 A1 | 1/2003 | Tanghoj et al. |
| 2003/0028174 A1 | 2/2003 | Chan et al. |
| 2003/0036802 A1 | 2/2003 | Lennox et al. |
| 2003/0055403 A1 | 3/2003 | Nestenborg et al. |
| 2003/0060807 A1 | 3/2003 | Tanghoj et al. |
| 2003/0065292 A1 | 4/2003 | Darouiche et al. |
| 2003/0130646 A1 | 7/2003 | Kubalak et al. |
| 2003/0132307 A1 | 7/2003 | Park |
| 2003/0135200 A1 | 7/2003 | Byrne |
| 2003/0163079 A1 | 8/2003 | Burnett |
| 2003/0195478 A1 | 10/2003 | Russo |
| 2003/0225392 A1* | 12/2003 | McMichael et al. ........ 604/509 |
| 2003/0233084 A1 | 12/2003 | Slepian et al. |
| 2004/0030301 A1 | 2/2004 | Hunter |
| 2004/0034329 A1 | 2/2004 | Mankus et al. |
| 2004/0044307 A1 | 3/2004 | Richardson et al. |
| 2004/0049152 A1 | 3/2004 | Nayak |
| 2004/0049170 A1 | 3/2004 | Snell |
| 2004/0055925 A1 | 3/2004 | Franks-Farah et al. |
| 2004/0059280 A1 | 3/2004 | Makower et al. |
| 2004/0068251 A1 | 4/2004 | Chan et al. |
| 2004/0074794 A1 | 4/2004 | Conway et al. |
| 2004/0116551 A1 | 6/2004 | Terry |
| 2004/0127848 A1 | 7/2004 | Freyman |
| 2004/0133156 A1 | 7/2004 | Diaz et al. |
| 2004/0147871 A1 | 7/2004 | Burnett |
| 2004/0153049 A1 | 8/2004 | Hewitt et al. |
| 2004/0153051 A1 | 8/2004 | Israelsson et al. |
| 2004/0158231 A1 | 8/2004 | Tanghoj et al. |
| 2004/0163980 A1 | 8/2004 | Tanghoj et al. |
| 2004/0176747 A1* | 9/2004 | Feneley ................ 604/544 |
| 2004/0243104 A1* | 12/2004 | Seddon ................ 604/540 |
| 2004/0249343 A1 | 12/2004 | Cioanta |
| 2004/0254562 A1 | 12/2004 | Tanghoj et al. |
| 2004/0256264 A1 | 12/2004 | Israelsson et al. |
| 2005/0015076 A1 | 1/2005 | Giebmeyer et al. |
| 2005/0031872 A1 | 2/2005 | Schmidt et al. |
| 2005/0033222 A1 | 2/2005 | Haggstrom et al. |
| 2005/0043715 A1 | 2/2005 | Nestenborg et al. |
| 2005/0049577 A1 | 3/2005 | Snell et al. |
| 2005/0059990 A1 | 3/2005 | Ayala et al. |
| 2005/0065499 A1 | 3/2005 | Douk et al. |
| 2005/0070882 A1 | 3/2005 | McBride |
| 2005/0080399 A1 | 4/2005 | Bolmsjo et al. |
| 2005/0096582 A1 | 5/2005 | Burnett |
| 2005/0101923 A1 | 5/2005 | Elson et al. |
| 2005/0101924 A1 | 5/2005 | Elson et al. |
| 2005/0107735 A1 | 5/2005 | Lennox et al. |
| 2005/0109648 A1 | 5/2005 | Kerzman et al. |
| 2005/0137522 A1 | 6/2005 | Aoki |
| 2005/0137582 A1 | 6/2005 | Kull-Osterlin et al. |
| 2005/0143690 A1 | 6/2005 | High |
| 2005/0148950 A1 | 7/2005 | Windheuser et al. |
| 2005/0197531 A1 | 9/2005 | Cabiri et al. |
| 2005/0199521 A1 | 9/2005 | Givens |
| 2005/0209580 A1 | 9/2005 | Freyman |
| 2005/0214443 A1 | 9/2005 | Madsen |
| 2005/0245901 A1 | 11/2005 | Floyd |
| 2005/0251108 A1 | 11/2005 | Frassica |
| 2005/0256447 A1 | 11/2005 | Richardson et al. |
| 2005/0273034 A1 | 12/2005 | Burnett |
| 2005/0283136 A1 | 12/2005 | Skarda |
| 2006/0025753 A1* | 2/2006 | Kubalak et al. ........ 604/544 |
| 2006/0027854 A1 | 2/2006 | Kim et al. |
| 2006/0030864 A1 | 2/2006 | Kennedy et al. |
| 2006/0036208 A1 | 2/2006 | Burnett |
| 2006/0041246 A1 | 2/2006 | Provost-tine et al. |
| 2006/0054557 A1 | 3/2006 | Hori et al. |
| 2006/0058777 A1 | 3/2006 | Nielsen |
| 2006/0064065 A1 | 3/2006 | Russo |
| 2006/0079835 A1 | 4/2006 | Frassica |
| 2006/0079854 A1 | 4/2006 | Kay et al. |
| 2006/0100511 A1 | 5/2006 | Eriksen |
| 2006/0122566 A1 | 6/2006 | Huang et al. |
| 2006/0122568 A1 | 6/2006 | Elson et al. |
| 2006/0163097 A1 | 7/2006 | Murray et al. |
| 2006/0172096 A1 | 8/2006 | Kyle et al. |
| 2006/0184112 A1 | 8/2006 | Horn et al. |
| 2006/0184145 A1 | 8/2006 | Ciok et al. |
| 2006/0196783 A1 | 9/2006 | Bruun et al. |
| 2006/0200079 A1* | 9/2006 | Magnusson ....... A61M 25/0017 604/164.1 |
| 2006/0263404 A1 | 11/2006 | Nielsen et al. |
| 2006/0271019 A1 | 11/2006 | Stoller et al. |
| 2006/0276894 A1 | 12/2006 | Finley |
| 2006/0278546 A1 | 12/2006 | State et al. |
| 2006/0293642 A1 | 12/2006 | Israelsson et al. |
| 2007/0005041 A1 | 1/2007 | Frassica et al. |
| 2007/0010798 A1 | 1/2007 | Stoller et al. |
| 2007/0016169 A1 | 1/2007 | Utas et al. |
| 2007/0049879 A1 | 3/2007 | Gutierrez |
| 2007/0066963 A1 | 3/2007 | Tanghoj |
| 2007/0106233 A1 | 5/2007 | Huang et al. |
| 2007/0112327 A1 | 5/2007 | Yun et al. |
| 2007/0149929 A1 | 6/2007 | Utas et al. |
| 2007/0197957 A1 | 8/2007 | Hunter et al. |
| 2007/0225635 A1 | 9/2007 | Lynn |
| 2007/0225649 A1* | 9/2007 | House ............... A61M 25/0017 604/171 |
| 2007/0225687 A1 | 9/2007 | House |
| 2007/0244449 A1 | 10/2007 | Najafi et al. |
| 2007/0289887 A1 | 12/2007 | Murray et al. |
| 2008/0006554 A1 | 1/2008 | Duffy et al. |
| 2008/0015518 A1 | 1/2008 | Huang et al. |
| 2008/0021382 A1 | 1/2008 | Freyman |
| 2008/0027414 A1 | 1/2008 | Tanghoj et al. |
| 2008/0033471 A1 | 2/2008 | Paz et al. |
| 2008/0050446 A1 | 2/2008 | Ziegler et al. |
| 2008/0051762 A1 | 2/2008 | Tsukada et al. |
| 2008/0051763 A1 | 2/2008 | Frojd |
| 2008/0077099 A1 | 3/2008 | House |
| 2008/0082051 A1 | 4/2008 | Miller et al. |
| 2008/0085949 A1* | 4/2008 | McGhee ..................... 523/149 |
| 2008/0091145 A1 | 4/2008 | House |
| 2008/0097362 A1 | 4/2008 | Mosler et al. |
| 2008/0097394 A1* | 4/2008 | Lampropoulos et al. .... 604/524 |
| 2008/0097411 A1 | 4/2008 | House |
| 2008/0140010 A1 | 6/2008 | Kennedy et al. |
| 2008/0140052 A1 | 6/2008 | Moller et al. |
| 2008/0171973 A1 | 7/2008 | House |
| 2008/0171998 A1 | 7/2008 | House |
| 2008/0172016 A1 | 7/2008 | House |
| 2008/0172042 A1 | 7/2008 | House |
| 2008/0179208 A1 | 7/2008 | Murray et al. |
| 2008/0200907 A1 | 8/2008 | Nestenborg |
| 2008/0243091 A1 | 10/2008 | Humphreys et al. |
| 2008/0249467 A1 | 10/2008 | Burnett et al. |
| 2008/0249482 A1 | 10/2008 | Erez |
| 2008/0275463 A1 | 11/2008 | High |
| 2009/0024111 A1 | 1/2009 | Borodulin et al. |
| 2009/0048537 A1 | 2/2009 | Lydon et al. |
| 2009/0054876 A1 | 2/2009 | Borodulin et al. |
| 2009/0065605 A1 | 3/2009 | Roche et al. |
| 2009/0071851 A1 | 3/2009 | Maki et al. |
| 2009/0099532 A1 | 4/2009 | Cuevas et al. |
| 2009/0131917 A1 | 5/2009 | Kavanagh et al. |
| 2009/0137985 A1 | 5/2009 | Tanghoej et al. |
| 2009/0137986 A1 | 5/2009 | Golden et al. |
| 2009/0149837 A1 | 6/2009 | Tanghoj et al. |
| 2009/0156882 A1 | 6/2009 | Chi Sing et al. |
| 2009/0200187 A1 | 8/2009 | Nestenborg et al. |
| 2009/0299334 A1 | 12/2009 | Nishtala et al. |
| 2009/0318900 A1 | 12/2009 | Tanghoj et al. |

(56) References Cited

U.S. PATENT DOCUMENTS

| | | |
|---|---|---|
| 2010/0263327 A1 | 10/2010 | Murray et al. |
| 2010/0324540 A1 | 12/2010 | Paulen et al. |
| 2011/0028943 A1 | 2/2011 | Lawson et al. |
| 2011/0056852 A1 | 3/2011 | Frojd |
| 2011/0114520 A1 | 5/2011 | Matthison-Hansen |
| 2011/0127186 A1 | 6/2011 | Enns et al. |
| 2011/0137296 A1 | 6/2011 | Tanghoj |
| 2011/0184386 A1 | 7/2011 | House |
| 2012/0168324 A1 | 7/2012 | Carleo |
| 2012/0316515 A1 | 12/2012 | Terry |
| 2013/0006226 A1 | 1/2013 | Hong et al. |
| 2013/0048516 A1 | 2/2013 | Nishtala et al. |
| 2013/0153446 A1 | 6/2013 | Utas et al. |
| 2013/0186778 A1 | 7/2013 | Terry |
| 2014/0262859 A1 | 9/2014 | Knapp et al. |
| 2015/0238726 A1 | 8/2015 | Terry |
| 2015/0273116 A1 | 10/2015 | Knapp et al. |
| 2017/0296704 A1 | 10/2017 | Knapp et al. |
| 2017/0326334 A1 | 11/2017 | Terry |

FOREIGN PATENT DOCUMENTS

| | | | |
|---|---|---|---|
| CN | 102939127 A | | 2/2013 |
| DE | 100 38 521 A1 | | 2/2002 |
| DE | 10213411 A1 | | 10/2003 |
| EP | 0217771 | | 4/1987 |
| EP | 0252918 A1 | | 1/1988 |
| EP | 247559 B1 * | 10/1990 | ............ A61M 25/01 |
| EP | 0479935 A1 | | 4/1992 |
| EP | 0677299 | | 10/1995 |
| EP | 0699086 A1 | | 3/1996 |
| EP | 0815037 A1 | | 1/1998 |
| EP | 0909249 A1 | | 4/1999 |
| EP | 0923398 | | 6/1999 |
| EP | 0935478 A1 | | 8/1999 |
| EP | 0959930 | | 12/1999 |
| EP | 0977610 A2 | | 2/2000 |
| EP | 1023882 | | 8/2000 |
| EP | 1090656 | | 4/2001 |
| EP | 1115450 A1 | | 7/2001 |
| EP | 1131022 A1 | | 9/2001 |
| EP | 1145729 | | 10/2001 |
| EP | 1175355 A1 | | 1/2002 |
| EP | 1237615 A1 | | 9/2002 |
| EP | 1245205 | | 10/2002 |
| EP | 1308146 | | 5/2003 |
| EP | 1406690 A2 | | 4/2004 |
| EP | 1409060 A2 | | 4/2004 |
| EP | 1420846 A1 | | 5/2004 |
| EP | 1420847 A2 | | 5/2004 |
| EP | 1427467 A2 | | 6/2004 |
| EP | 1498151 | | 1/2005 |
| EP | 1629860 | | 3/2006 |
| EP | 1641510 A1 | | 4/2006 |
| EP | 1642610 | | 4/2006 |
| EP | 1642611 | | 4/2006 |
| EP | 2060296 A1 | | 5/2009 |
| EP | 2459264 A1 | | 6/2012 |
| EP | 2464411 A1 | | 6/2012 |
| EP | 2515988 A1 | | 10/2012 |
| EP | 2542291 A1 | | 1/2013 |
| EP | 3078393 B1 | | 11/2017 |
| EP | 2967968 B1 | | 9/2018 |
| FR | 2731345 A1 | | 9/1996 |
| FR | 2 794 638 A1 | | 12/2000 |
| GB | 2284764 | | 6/1995 |
| GB | 2319507 | | 5/1998 |
| JP | S55-12265 B2 | | 3/1980 |
| JP | 2001-500414 A | | 1/2001 |
| JP | 2002-530148 A | | 9/2002 |
| JP | 2002 282275 A | | 10/2002 |
| JP | 2007-501656 A | | 2/2007 |
| JP | 2011-510110 A | | 3/2011 |
| JP | 2013-500125 | | 1/2013 |
| JP | 2013-515572 | | 5/2013 |
| WO | 198401296 A1 | | 4/1984 |
| WO | 1986006284 | | 11/1986 |
| WO | 1991005577 A1 | | 5/1991 |
| WO | 1994016747 A1 | | 8/1994 |
| WO | 1996038192 A1 | | 12/1996 |
| WO | 1997026937 | | 7/1997 |
| WO | 1997041811 | | 11/1997 |
| WO | 1998006642 | | 2/1998 |
| WO | 1998011932 | | 3/1998 |
| WO | 1998019729 | | 5/1998 |
| WO | 98/46176 A1 | | 10/1998 |
| WO | 1999030761 A1 | | 6/1999 |
| WO | 2000016843 | | 3/2000 |
| WO | 2000047494 | | 8/2000 |
| WO | 2001043807 | | 6/2001 |
| WO | 2001052763 | | 7/2001 |
| WO | 2001093935 | | 12/2001 |
| WO | 2002036192 | | 5/2002 |
| WO | 2003002177 | | 1/2003 |
| WO | 2003002178 | | 1/2003 |
| WO | 2003008028 | | 1/2003 |
| WO | 2003008029 | | 1/2003 |
| WO | 2003064279 A1 | | 8/2003 |
| WO | 2003092779 | | 11/2003 |
| WO | 2004030722 | | 4/2004 |
| WO | 2004045696 | | 6/2004 |
| WO | 2004045696 A1 | | 6/2004 |
| WO | 2004050155 | | 6/2004 |
| WO | 2004052440 | | 6/2004 |
| WO | 2004056414 | | 7/2004 |
| WO | 2004075944 | | 9/2004 |
| WO | 2004089454 | | 10/2004 |
| WO | 2005004964 | | 1/2005 |
| WO | 2005014055 A2 | | 2/2005 |
| WO | 2005061035 | | 7/2005 |
| WO | 2005092418 | | 10/2005 |
| WO | 2007050685 | | 5/2007 |
| WO | 2007050685 A2 | | 5/2007 |
| WO | 2009012336 A1 | | 1/2009 |
| WO | 2007050685 A3 | | 4/2009 |
| WO | 2011014201 A1 | | 2/2011 |
| WO | 2011019359 A1 | | 2/2011 |
| WO | 2011063816 A1 | | 6/2011 |
| WO | 2011079129 A1 | | 6/2011 |
| WO | 2011109393 A1 | | 9/2011 |
| WO | 2014165046 A1 | | 10/2014 |

OTHER PUBLICATIONS

PCT/US2009/055395 filed Aug. 28, 2009 International Preliminary Report on Patentability dated Jan. 31, 2012.

PCT/US2009/055395 filed Aug. 28, 2009 International Search Report dated Oct. 15, 2009.

PCT/US2009/055395 filed Aug. 28, 2009 Written Opinion dated Oct. 15, 2009.

EP 09848341.5 filed Feb. 27, 2012 extended European Search Report dated Apr. 4, 2013.

PCT/US2006/041633 filed Oct. 25, 2006 International Preliminary Report on Patentability dated Mar. 24, 2009.

PCT/US2006/041633 filed Oct. 25, 2006 Search Report dated Aug. 12, 2008.

PCT/US2006/041633 filed Oct. 25, 2006 Written Opinion dated Aug. 12, 2008.

PCT/US2009/055389 filed Aug. 28, 2009 International Search Report dated Oct. 20, 2009.

PCT/US2009/055389 filed Aug. 28, 2009 Written Opinion dated Oct. 20, 2009.

PCT/US2010/061597 filed Dec. 21, 2010 International Preliminary Report on Patentability dated Jun. 26, 2012 and Written Opinion dated Feb. 28, 2011.

PCT/US2010/061597 filed Dec. 21, 2010 International Search Report dated Feb. 28, 2011.

PCT/US2011/026681 filed Mar. 1, 2011 International Preliminary Report on Patentability dated Sep. 4, 2012.

PCT/US2011/026681 filed Mar. 1, 2011 International Search Report dated Apr. 27, 2011.

(56) References Cited

OTHER PUBLICATIONS

PCT/US2011/026681 filed Mar. 1, 2011 Written Opinion dated Apr. 27, 2011.
U.S. Appl. No. 12/091,916, filed Feb. 2, 2009 Final Office Action dated Sep. 22, 2011.
U.S. Appl. No. 12/091,916, filed Feb. 2, 2009 Non-Final Office Action dated May 10, 2011.
U.S. Appl. No. 12/091,916, filed Feb. 2, 2009 Non-Final Office Action dated Nov. 24, 2010.
U.S. Appl. No. 12/091,916, filed Feb. 2, 2009 Notice of Allowance dated Aug. 17, 2012.
EP 10840071.4 filed Jul. 4, 2012 extended European Search Report dated Apr. 17, 2013.
EP 11751198.0 filed Sep. 28, 2012 extended European search report dated Jul. 9, 2013.
CA 2,769,026 filed Jan. 24, 2012 First Examination Report dated Nov. 4, 2013.
EP 09848341.5 filed Feb. 27, 2012 supplemental European Search Report dated Nov. 8, 2013.
EP 11751198.0 filed Sep. 28, 2012 Exam Report dated Feb. 7, 2014.
CN 201080058895.4 filed Jun. 21, 2012 First Office Action dated Feb. 27, 2014.
EP 10840071.4 filed Jul. 4, 2012 Exam Report dated Apr. 29, 2014.
JP 2012-546157 filed Jun. 12, 2012 First Office Action dated Sep. 16, 2014.
PCT/US2014/024231 filed Mar. 12, 2014 International Search Report and Written Opinion dated Jul. 10, 2014.
U.S. Appl. No. 13/389,753, filed Mar. 20, 2012 Non-Final Office Action dated Jul. 21, 2014.
U.S. Appl. No. 13/802,095, filed Mar. 13, 2013 Non-Final Office Action dated Aug. 15, 2014.
CN 201080058895.4 filed Jun. 21, 2012 Second Office Action dated Nov. 3, 2014.
CN 201080058895.4 filed Jun. 21, 2012 Third Office Action dated May 4, 2015.
U.S. Appl. No. 13/389,753, filed Mar. 20, 2012 Final Office Action dated Dec. 10, 2014.
U.S. Appl. No. 13/582,698, filed Sep. 4, 2012 Non-Final Office Action dated Sep. 24, 2014.
U.S. Appl. No. 13/662,278, filed Oct. 26, 2012 Final Office Action dated Feb. 20, 2015.
U.S. Appl. No. 13/662,278, filed Oct. 26, 2012 Non-Final Office Action dated Sep. 12, 2014.
U.S. Appl. No. 13/802,095, filed Mar. 13, 2013 Notice of Allowance dated Nov. 28, 2014.
"Tripartite Biocompatibility Guidance for Medical Devices," DSMA (Apr. 24, 1987).
EP 14779919.1 filed Sep. 10, 2015 Extended European Search Report dated Aug. 23, 2016.
EP 16171279.9 filed May 25, 2016 Extended European Search Report, dated Aug. 23, 2016.
Norton, J.A. et al., Surgery: Basic Science and Clinical Evidence Springer, 2nd ed., 2008, p. 281.
U.S. Appl. No. 13/516,660, filed Aug. 27, 2012 Final Office Action dated Jun. 29, 2016.
U.S. Appl. No. 13/662,278, filed Oct. 26, 2012 Non-Final Office Action dated Jul. 7, 2016.
U.S. Appl. No. 13/516,660, filed Aug. 27, 2012 Non-Final Office Action dated Mar. 8, 2016.
BR PI 0506836-3 filed Jan. 18, 2005, Technical Report dated Jul. 28, 2015.
EP 10840071.4 filed Jul. 4, 2012 Office Action dated Jul. 9, 2015.
JP 2012-546157 filed Jun. 12, 2012 Decision of Rejection dated Aug. 21, 2015.
U.S. Appl. No. 13/389,753, filed Mar. 20, 2012 Examinees Answer dated Aug. 27, 2015.
U.S. Appl. No. 13/662,278, filed Oct. 26, 2012 Non-Final Office Action dated Sep. 17, 2015.
EP 17201044.9 filed Nov. 10, 2017 Extended European Search Report dated Jan. 18, 2018.
JP 2016-501444 filed Sep. 11, 2015 Office Action dated Dec. 14, 2017.
U.S. Appl. No. 13/516,660, filed Aug. 27, 2012 Examiner's Answre dated Nov. 22, 2017.
CN 201480013064.3 filed Sep. 8, 2015 Office Action dated Oct. 10, 2016.
JP 2015-243156 filed Dec. 14, 2015 Office Action dated Sep. 16, 2016.
U.S. Appl. No. 13/516,660, filed Aug. 27, 2012 Advisory Action dated Sep. 22, 2016.
U.S. Appl. No. 13/662,278, filed Oct. 26, 2012 Final Office Action dated Oct. 19, 2016.
CN 201480013064.3 filed Sep. 8, 2015 Office Action dated Jun. 29, 2017.
EP 10840071.4 filed Jul. 4, 2012 Notice of Opposition dated Apr. 24, 2017.
EP 14779919.1 filed Sep. 10, 2015 Office Action dated Jul. 4, 2017.
EP 16171279.9 filed May 25, 2016 Intent to Grant, dated Jun. 13, 2017.
U.S. Appl. No. 13/389,753, filed Mar. 20, 2012 Decision on Appeal dated Jun. 29, 2017.
U.S. Appl. No. 13/389,753, filed Mar. 20, 2012 Notice of Allowance dated Jul. 5, 2017.
U.S. Appl. No. 13/662,278, filed Oct. 26, 2012 Examinees Answer dated Jun. 2, 2017.
U.S. Appl. No. 13/662,278, filed Oct. 26, 2012 Board Decision dated Aug. 23, 2018.

\* cited by examiner

CATHETER HAVING IMPROVED DRAINAGE AND/OR A RETRACTABLE SLEEVE AND METHOD OF USING THE SAME

CROSS REFERENCE TO RELATED APPLICATIONS

This application is a U.S. national stage application under 35 U.S.C. § 371 of International Application No. PCT/US2009/055395, filed Aug. 28, 2009, claiming priority to U.S. Provisional Application No. 61/229,563, filed Jul. 29, 2009, each of which is incorporated by reference in its entirety into this application.

STATEMENT CONCERNING GOVERNMENT INTEREST

Not applicable.

BACKGROUND OF THE INVENTION

Intermittent catheterization is a sterile process of draining urine from the bladder when normal draining is impossible or difficult. Proper intermittent catheter use reduces the risk of urinary tract infections and kidney damage. Intermittent catheters come in many different sizes and lengths to fit the body. Some catheters are also available pre-lubricated.

Intermittent catheterization is generally performed a minimum of four times a day by the patient or a care giver. The genital area near the urethral opening is wiped with an antiseptic agent, such as iodine. A lubricant may then be used to facilitate the entry of the catheter into the urethra. A topical local anesthetic may also be applied to numb the urethral opening during the procedure. One end of the catheter is placed in a container, and the other end is inserted into and guided up the urethra and into the bladder until urine flow begins.

When urine flow stops, the catheter may be re-positioned, moved or rotated. The patient may also be made to change positions to ensure that all urine has emptied from the bladder. The catheter may then be withdrawn, cleaned, and sterilized for the next use. Recommended cleaning practices vary, from the use of soap and water, to submersion in boiling water or a disinfectant solution. Some patients prefer to use a new catheter with each insertion or catheterization.

Intermittent catheters are generally catheters or tubes having a rounded, atraumatic distal tip that is inserted into the bladder of a patient. A molded funnel is typically connected to a distal end that remains outside the body of the patient or user. The distal tip may include slots or openings on the shaft to facilitate drainage of urine therefrom once the tip is positioned inside the bladder.

Pre-wetted intermittent catheters are intermittent catheters having a highly lubricious coating on an outer surface thereof, which are packaged or otherwise brought into contact with fluid in order to provide a catheter with a slippery outer surface to facilitate insertion into the patient or user.

Existing pre-wetted intermittent catheters fall into three broad categories. In a first type, the catheter is packaged in a dry environment, but it contains a lubricious coating that requires a wetting fluid in order to become hydrated. The wetting fluid is obtained from an external source by the user (e.g., sink, bottled water, etc.), and the catheter is positioned within the wetting fluid for a period of time to become hydrated. Use of this first type of intermittent catheter may prove difficult where no clean water or wetting fluid is readily available. Moreover, catheter sterility may be compromised due to the user's handling of the catheter when wetting fluid is applied.

A second type of pre-wetted intermittent catheter is also packaged in a dry environment and contains a lubricious coating. However, the wetting fluid is positioned in a pouch or container within the catheter package itself. To hydrate the catheter, the pouch or container is opened when the user is ready for insertion. Suitable examples of such catheters are disclosed in U.S. Pat. No. 7,087,048 (the disclosure of which is incorporated herein by reference in its entirety). As with the first type, this second type may be disadvantageous because the catheter is exposed to the wetting fluid for a period of time to ensure hydration of the lubricious coating. The sterility of the catheter may also be compromised during insertion.

A third type of pre-wetted intermittent catheter is packaged in a wet environment. That is, the catheter is exposed to a wetting fluid within the catheter package, thus hydrating the coating. However, the user may have difficulty handling the catheter due to its slippery surface, and excessive or imprecise handling may result in contamination of the catheter by the user. This could then expose the user to a urinary tract infection.

Existing intermittent catheters also drain urine into a bag. Following bladder drainage into the bag, the bag may be emptied by inverting and tearing a notch. Urine is then drained into a receptacle through the tear. That process can be slow, messy, and subject to urine spills.

Non-intermittent catheterization, which is used in a hospital or nursing home setting, uses the same basic technique for insertion of the urinary tract catheter. The catheter is inserted by a nurse or other health care professional, and, it remains in the patient until bladder function can be maintained independently. When the catheter is removed, patients experience a pulling sensation and may feel some minor discomfort. If the catheter is required for an extended period of time, a long-term, indwelling catheter, such as a Foley catheter, is used. To prevent infection, it should be regularly exchanged for a new catheter every three to six weeks.

Proper catheter use can also often be determined by the length of time that the process is necessary: long-term (often called indwelling) or short-term use. In some situations, incontinent patients are catheterized to reduce their cost of care. A condom catheter, which fits on the outside of the penis using adhesive, can be used for short-term catheterization in males. However, long-term catheterization is not recommended because chronic use carries a significant risk of urinary tract infection. This risk catheterization should only be considered as a last resort for the management of incontinence where other measures have proved unsuccessful and where there is significant risk to the skin.

A catheter that is left in place for a period of time may be attached to a drainage bag to collect the urine. There are two types of drainage bags. One is a leg bag being a smaller drainage device that attaches by elastic bands to the leg. A leg bag is usually worn during the day, as it fits discreetly under pants or skirts, and is easily emptied into a toilet. The second type of drainage bag is a larger device called a down drain that may be used during the night. This device is usually hung on the patient's bed or placed on the floor nearby.

During long-term use, the catheter may be left in place the entire duration, or a patient may be instructed on a intermittent self-catheterization procedure for placing a catheter just long enough to empty the bladder and then removing it.

Patients undergoing major surgery are often catheterized and may remain so for long durations. Long-term catheterization can expose patients to an increased risk of infection. Long-term catheterization as a remedy for incontinence is not appropriate, as the risks outweigh the benefits.

In males, for example, the catheter tube is inserted into the urinary tract through the penis. A condom catheter can also be used. In females, the catheter is inserted into the urethral meatus, after a cleansing using povidone-iodine. The procedure can be complicated in females due to varying layouts of the genitalia (due to age, obesity, Female genital cutting, childbirth, or other factors), but a good clinician should rely on anatomical landmarks and patience when dealing with such a patient.

Common indications to catheterize a patient include acute or chronic urinary retention (which can damage the kidneys), orthopedic procedures that may limit a patient's movement, the need for accurate monitoring of input and output (such as in an ICU), benign prostatic hyperplasia, incontinence, and the effects of various surgical interventions involving the bladder and prostate.

For some patients the insertion and removal of a catheter can cause excruciating pain, so a topical anesthetic can be used for patients of both sexes. Catheterization should be performed as a sterile medical procedure and should only be done by trained, qualified personnel, using equipment designed for this purpose. However, in the case of intermittent self catheterization, the patient can perform the procedure his/her self. If correct technique is not used, trauma may be caused to the urethra or prostate (male). A urinary tract infection or paraphimosis may also occur (male uncircumcised patient).

Particular complications of catheter use may include: urinary tract or kidney infections, blood infections (sepsis), urethral injury, skin breakdown, bladder stones, and blood in the urine (hematuria). After many years of catheter use, bladder cancer may also develop. In using indwelling (long-term) catheters, it is particularly very important to take everyday care of the catheter and the drainage bag.

Catheters come in a large variety of sizes, materials (latex, silicone, PVC, or Teflon), and types (Foley catheter, straight catheter, or coude tip catheter). In the case of internal catheters, those inserted into the urethra, the smallest size is usually recommended, although a larger size is sometimes needed to control leakage of urine around the catheter. A large size can also become necessary when the urine is thick, bloody or contains large amounts of sediment. Larger internal catheters, however, are more likely to cause damage to the urethra. Some people develop allergies or sensitivities to latex after long-term latex catheter use. In such cases, silicone or Teflon types should be used. Silver alloy coated urinary catheters may reduce infections.

Catheter diameters are sized by the French catheter scale (F). The most common sizes are 10 F to 28 F. The clinician selects a size large enough to allow free flow of urine, but large enough to control leakage of urine around the catheter. A larger size can become necessary when the urine is thick, bloody or contains large amounts of sediment. Larger catheters, however, are more likely to cause damage to the urethra. (Jeffrey A N et al., Surgery: Basic Science and Clinical Evidence Springer, 2nd ed., 2008, p. 281).

Catheters are regulated as class II medical devices under section 513 of the Federal Food, Drug, and Cosmetic Act (the act) and the appropriate panel (78 Gastroenterology/Urology) as described in 21 CFR 807.87(c).

Finally, it is noted that existing intermittent catheters typically have two staggered drainage eyelets or openings which are located on a distal end of the catheter, i.e., near the inserting tip. These openings limit the draining ability of the catheter.

SUMMARY OF THE INVENTION

The present invention is directed to easy-to-use urinary catheter assemblies that eliminate or minimize some of the shortcomings of prior art devices. The catheter can be a single-use catheter and/or may be packaged as a single-use device. Non-limiting embodiments of the invention include one or more features described herein and/or shown in the drawings in combination with one of more prior art features discussed above.

Non-limiting embodiments of the invention provide for improved drainage by utilizing an array of staggered drainage eyelets or openings on the catheter.

Non-limiting embodiments of the invention also provide for improved drainage by utilizing a single enlarged drainage eyelet or opening on the catheter.

Non-limiting embodiments of the invention also provide for a catheter tip having an opening which can be a generally coaxial opening, a council opening, and/or a guide opening. This opening can allow a small amount of urine to pass through the catheter so as to provide an indication to the user that the catheter is properly positioned within the bladder. This opening can also receive a guide wire to facilitate catheterization.

Non-limiting embodiments of the invention also provide for a catheter having a retractable sleeve arranged thereon. Preferably, the sleeve is a lubricious sleeve which can be moved from a first or initial position wherein the sleeve covers the drainage openings to a second or retracted position wherein the sleeve does not cover the drainage openings.

Non-limiting embodiments of the invention also provide for a catheter having a retractable sleeve arranged thereon which can be moved by the user or patient while the catheter is inserted into the bladder.

Non-limiting embodiments of the invention also provide for a method of inserting a catheter of the type described herein which includes inserting the catheter having a retractable sleeve into a user's body, and retracting the sleeve to expose drainage openings and drain a fluid from the user's body. The fluid can be urine and the method can also include determining that a catheter tip is properly and/or fully inserted into the bladder.

Non-limiting embodiments of the invention also provide for a method of draining a bladder using the catheter of the type described herein which can include inserting the catheter having a retractable sleeve into the bladder, providing an indication that a catheter tip is properly and/or fully inserted into the bladder, and retracting the sleeve to expose the drainage openings and drain urine from the bladder.

Non-limiting embodiments of the invention also provide for a method of draining a bladder using the catheter of the type described herein which can include guiding with a guide wire the catheter having a retractable sleeve into the bladder, and retracting the sleeve to expose the drainage openings and drain urine from the bladder. The method can also include providing an indication that a catheter tip is properly and/or fully inserted into the bladder.

The invention also provides for a catheter comprising an elongate member having a proximal end and a distal end. The distal end has at least one drainage opening. At least one of the at least one drainage opening comprises a single elongate opening, the at least one drainage opening comprises two circumferentially spaced elongate openings, the at least one drainage opening comprises at least three staggered openings, the at least one drainage opening comprises an array of staggered openings, and a sleeve member is arranged on the elongate member and is movable at least between a first position covering the at least one drainage opening and a second position which allows fluid to pass into the catheter.

The catheter may comprise the sleeve member and the sleeve member further comprises a distal end that facilitates gripping by a user. The catheter may comprise the sleeve member and the sleeve member further comprises one of a hydrateable coating arranged at least on an outer surface of a distal end of the sleeve member, a lubricious coating arranged at least on an outer surface of a distal end of the sleeve member, and a hydrophilic biocompatible coating arranged at least on an outer surface of a distal end of the sleeve member. The catheter may be an intermittent catheter.

The catheter may comprise the single elongate opening and the single elongate opening may be an elongate oval-shaped opening. The catheter may comprise the at least three staggered openings and each of the staggered opening may be generally oval-shaped. The catheter may comprise the array of staggered openings and each staggered opening may be generally oval-shaped. The catheter may comprise the two circumferentially spaced elongate openings and each elongate opening may be generally oval-shaped. The catheter may comprise the sleeve member and the sleeve member may further comprise a lubricious antimicrobial coating arranged at least on an outer surface of a distal end of the sleeve member. The catheter may further comprise a pre-draining opening arranged on the distal end of the elongate member. The catheter may further comprise a sealing member arranged to provide sealing between the sleeve member and the elongate member.

The elongate member may comprise one of a hydrateable coating arranged at least on an outer surface of the distal end of the elongate member, a lubricious coating arranged at least on an outer surface of the distal end of the elongate member, and a hydrophilic biocompatible coating arranged at least on an outer surface of the distal end of the elongate member. The elongate member may comprise a tip having an opening. The opening may be one of a generally coaxial opening, a council opening, a guide opening, and a guide wire receiving opening. The opening may be configured to allow a small amount of urine to pass through the catheter so as to provide an indication to the user that the catheter is properly positioned within a bladder. The opening may be configured to receive a guide wire to facilitate catheterization. The catheter may comprise the sleeve member and the sleeve member may be capable of being moved by the user or patient while the catheter is inserted into the bladder.

The invention also provides for a method of inserting the catheter of the type described above, wherein the method comprises inserting the catheter sleeve into a user's body and retracting the sleeve member to expose drainage openings and drain a fluid from the user's body.

The fluid may be urine. The method may further comprise determining that a catheter tip is properly and/or fully inserted into the bladder.

The invention also provides for a method of draining a bladder using the catheter of the type described above, wherein the method comprises inserting a catheter having a retractable sleeve into the bladder, providing an indication that a catheter tip is properly and/or fully inserted into the bladder, and retracting the retractable sleeve to expose drainage openings and drain urine from the bladder.

The invention also provides for a method of draining a bladder using the catheter of the type described above, wherein the method comprises guiding with a guide wire the catheter having a retractable sleeve into the bladder and retracting the retractable sleeve to expose drainage openings and drain urine from the bladder.

The method may further comprise providing an indication that a catheter tip is properly and/or fully inserted into the bladder.

The invention also provides for a catheter comprising an elongate member having a proximal end and a distal end. The distal end has at least one of a single elongate drainage opening, two circumferentially spaced elongate drainage openings, at least three staggered drainage openings, and an array of staggered drainage openings. A sleeve member is arranged and/or movably disposed on the elongate member and has a gripping member. The sleeve member is insertable with the elongate member into a user's body and is movable at least between a first position preventing fluid from passing into the catheter and a second position which allows fluid to pass into the catheter.

The invention also provides for a catheter comprising an elongate member having a proximal end and a distal end. The distal end has at least one drainage opening. At least one of the at least one drainage opening comprises a single elongate opening, the at least one drainage opening comprises at least three staggered openings, and the at least one drainage opening comprises an array of staggered openings. A movable sleeve member is arranged on the elongate member. The sleeve member may be insertable with the elongate member into a user's body and is movable at least between a first position preventing fluid from passing into the distal end of the elongate member and a second position which allows fluid to pass into the distal end of the elongate member.

The sleeve member may be movable at least between a first position covering the at least one drainage opening and a second position which exposes all of the at least one drainage opening. The sleeve member may comprise a distal end that facilitates gripping by a user. The sleeve member may further comprise one of a hydrateable coating arranged at least on an outer surface of a distal end of the sleeve member, a lubricious coating arranged at least on an outer surface of a distal end of the sleeve member, and a hydrophilic biocompatible coating arranged at least on an outer surface of a distal end of the sleeve member. The catheter may be an intermittent catheter.

The elongate member may comprise a lubricious antimicrobial coating arranged at least on an outer surface of the distal end of the elongate member and the sleeve member may comprise a lubricious antimicrobial coating arranged at least on an outer surface of a distal end of the sleeve member.

The invention also provides for a method of draining a bladder using the catheter described above, wherein the method comprises inserting a catheter having a retractable sleeve into the bladder, providing an indication to the user that a catheter tip is properly and/or fully inserted into the bladder, and retracting the retractable sleeve to expose drainage openings and drain urine from the bladder.

The invention also provides for a method of draining a bladder using the catheter described above, wherein the method comprises guiding with a guide wire the catheter having a retractable sleeve into the bladder and retracting the retractable sleeve to expose drainage openings and drain urine from the bladder.

BRIEF DESCRIPTION OF DRAWINGS OF THE EXEMPLARY EMBODIMENTS

DETAILED DESCRIPTION OF THE EXEMPLARY EMBODIMENTS

The following description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will enable one skilled in the art to make and use the invention, and describes several embodiments, adaptations, variations, alternatives and uses of the invention, including what is presently believed to be the best mode of carrying out the invention.

As used herein, the reference terms "proximal" and "distal" (proximal being closer than distal) refer to proximity with respect to a health care professional catheterizing a patient. For example, the region or section of the catheter apparatus that is closest to the health care professional during catheterization is referred to herein as "proximal," while a region or section of the catheter apparatus closest to the patient's bladder is referred to as "distal." In the case of a self-catheterizing patient, proximal refers to a point external to the patient's body, and distal refers to a point within the patient's body (i.e., the bladder).

The catheter assemblies as described herein are discussed in the context of a urinary catheter for insertion into a bladder for drainage of urine therefrom. The instant catheter assemblies, however, may also be used for other applications not specifically mentioned herein. As such, the instant invention is not limited to urinary catheter applications.

Figure 1:
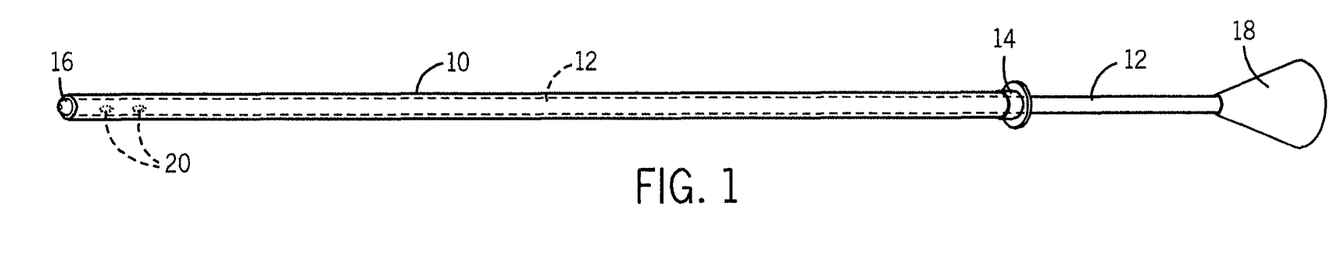
FIG. 1 shows an intermittent elongate catheter or catheter system in a closed/extended/original/pre-use configuration.
Figure 2:
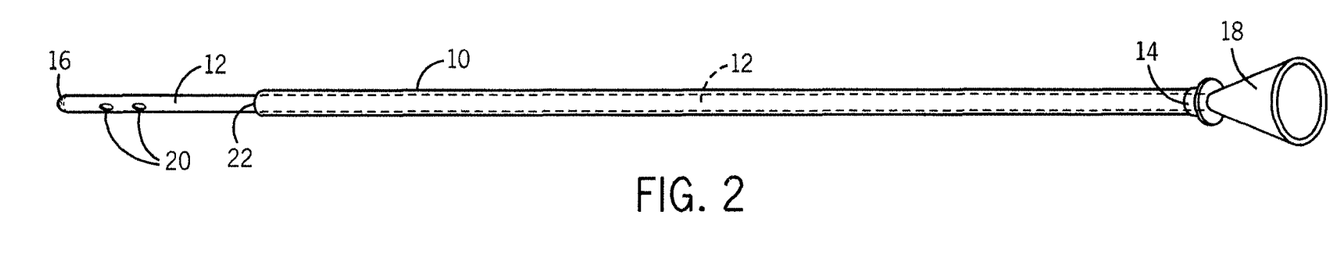
FIG. 2 shows the intermittent elongate catheter of FIG. 1 in an open/retracted/use configuration.

FIGS. 1 and 2 show a non-limiting embodiment of an elongate urinary intermittent catheter of the present invention. FIG. 1 shows the catheter in a closed/extended/original/initial configuration whereas FIG. 2 shows the catheter in an open/retracted/using/locked configuration.

The assembly shown in FIG. 1 can be inserted into a user's body until the distal end is safely positioned in the bladder. Thereafter, the sleeve can be retracted to place the catheter into the position shown in FIG. 2. In this way, fluid from the bladder can drain through the catheter. A substantially portion of the outer surface of the distal end of the catheter shown in FIG. 1 can include a lubricious coating to facilitate insertion of the catheter into the user's body.

The catheter includes an elongate member 12 having proximal and distal ends. The elongate member 12 can have any size and shape typically utilized in conventional catheters such as generally cylindrical and defines an interior lumen or space which allows fluid to pass and/or drain through. The proximal end includes a funnel 18 which can be of any type that is typically utilized in catheters. The funnel 18 can be connected to any type fluid collection system or bag that is typically utilized in catheters. By way of non-limiting example, the funnel 18 can be a rubber or plastic drainage funnel 18 disposed and friction-fitted on the proximal end of the member 12. A disposable bag (not shown) may be disposed on and/or coupled to the drainage funnel 18 to collect the patient's urine. The distal end of member 12 also includes a tip 16. The tip 16 is arranged on a forward most portion of the distal end and defines the insertion end of the catheter. The elongate member 12 also preferably contains a biocompatible, hydrophillic, antimicrobial and/or lubricious coating on its outer surface (not shown).

A sleeve member 10 is arranged on the elongate member 12. The sleeve member 10 has proximal and distal ends. The proximal end has a gripping portion 14 arranged thereon and the distal end 22 is capable of moving between the positions shown in FIGS. 1 and 2. The sleeve member 10 can have any size and shape, but preferably generally corresponds to that of the member 12. The sleeve member 10 can be generally cylindrical and defines an interior lumen or space which receives therein (with some clearance) the elongate member 12. The sleeve 10 can also be substantially transparent or translucent. The dotted lines in FIGS. 1 and 2 represent the inner and outer diameter surfaces of the member 12 and the sleeve 10 respectively. The sleeve 10 also preferably has a biocompatible, hydrophillic, antimicrobial and/or lubricious coating on its outer surface (not shown). The coating can facilitate insertion of the catheter. The coating can also be utilized to increase drainage efficiency and reduce propensity of residual urine in the bladder after voiding.

A gripping portion or grommet 14 is arranged on the proximal end of the sleeve 10. The portion 14 can also include function to provide a sealing engagement between the member 12 and sleeve 10. This sealing engagement can be provided by sizing an internal diameter of the member 14 to substantially match (i.e., substantially no clearance) that of the member 12 or by arranging a sealing member in the member 14 to seal sleeve 10 with respect to the member 12. A flange/hub structure or portion of the member 14 allows the patient or medical personnel to grip or grab the sleeve 10 and move it axially relative to the member 12.

Figure 3:
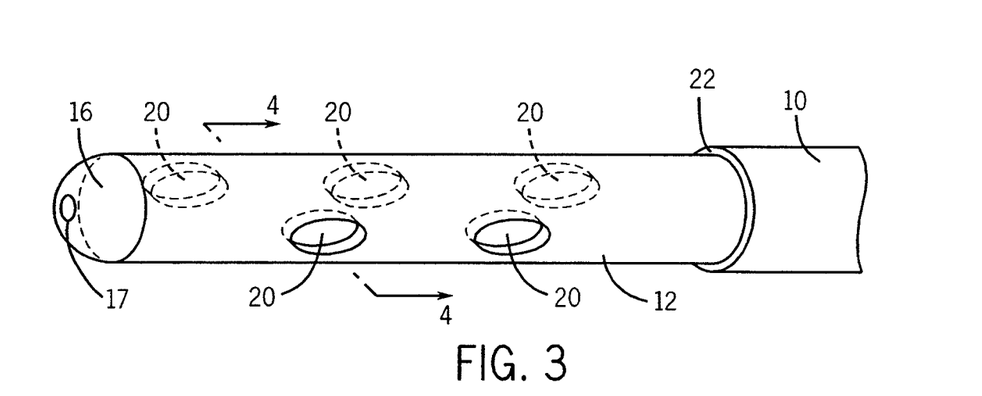
FIG. 3 shows the multiple eyelets or openings disposed at the distal end of the conduit, whereby the conduit is in an extended configuration opening the eyelets.
Figure 4:
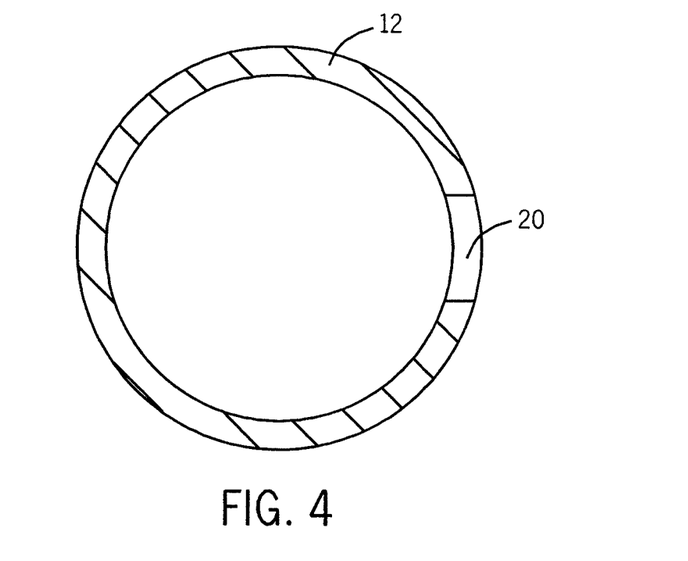
FIG. 4 shows a cross-sectional view of the intermittent elongate catheter in the open/extended configuration of FIG. 3 near the distal end of the conduit.

With reference to FIGS. 3 and 4, it can be seen that the distal end of the member 12 can include an array of staggered drainage eyelet-shaped apertures or openings 20. Preferably, the openings 20 are staggered, i.e., they have center axes which are axially spaced and/or are also circumferentially spaced from each other, to facilitate flow into and through the member 12. By way of non-limiting example, the axial spacing between the openings 20 can be between an amount that is about a diameter of each opening and an amount equal to about twice the diameter of each opening. By way of non-limiting example, the circumferential spacing between the openings 20 can be between about 90 degrees and about 180 degrees. These openings 20 allow entry of fluid or urine from the patient's body into the member 12. Thus occurs, for example, when the member 12 is inserted into a bladder. The plurality of apertures 20 also provide enhanced flexibility at the distal end of the member 12, which makes the catheter more comfortable for the patient. The eyelets or openings 20 may be of any suitable size, shape, configuration and/or number so as to provide for entry of the patient's urine upon insertion into the patient's urethra, i.e., generally the first third of the urethra. In the closed/initial configuration shown in FIG. 1, the eyelets 20 are closed off by virtue of the distal end 22 of the sleeve 10 being in a position which covers all of the openings 20. In this way, the outer surface of the sleeve 10 covers and substantially seals the eyelets or openings 20. This sealing can occur using the frictional engagement between an inside diameter of the sleeve 10 relate to an outer diameter of the member 12 or alternatively via a seal arranged on an inside diameter of the end 22 (not shown). A lubricious coating can be arranged on either an inside diameter of the sleeve 10 and/or an outer diameter of the member 12 to, among other things, facilitate the relative movement of the sleeve 10 relative to the member 12 between the positions shown in FIGS. 1 and 2.

Again, with reference to FIG. 3 it can be seen that the tip 16 can preferably include a council or guide wire hole 17. This hole 17 can be substantially centrally disposed and can function to, e.g., provided as a way of verifying that the tip 16 has entered the patient's bladder. Once the tip 16 enters the bladder (even with the openings 20 closed off), a small amount of the patient's urine enters the council hole 17 and starts to flow into the catheter or member 12 and out of the funnel 18. This provides an indication to the patient or medical personnel that the catheter is fully or properly inserted into the bladder. The user can then pull back on the sleeve 10 so as to open the eyelets 20 and insert the member 12 a little further into the bladder. The council hole 17 can also be used to track or guide the catheter over an accessory guide wire (not shown) for patients that are difficult to catheterize.

Figure 5:
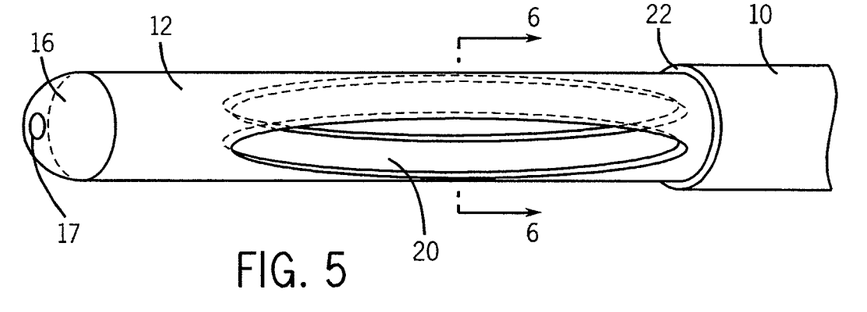
FIG. 5 shows the intermittent elongate catheter in the open/extended configuration, whereby two elongate eyelets are shown near the distal end of the conduit.
Figure 6:
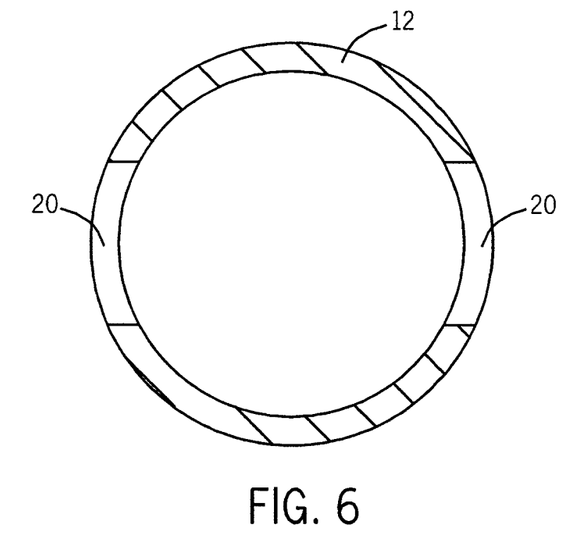
FIG. 6 shows a cross-sectional view of the intermittent elongate catheter in the open/extended configuration of FIG. 5 near the distal end of the conduit.

FIGS. 5 and 6 show an alternative configuration for the distal end of the elongate member 12. In place of the array of staggered openings shown in FIGS. 3 and 4, the distal end includes instead two generally oppositely, i.e., about 180 degrees apart, arranged elongate eyelets 20 disposed near the distal end of the member 12. Although not shown, these openings 20 can also be arranged axially offset from one another.

The member 12 and sleeve 10 may have a round cross-sectional shape, an oval cross-sectional shape, or any other cross-sectional shape that may facilitate insertion into the body of a user/patient, and, in particular, into the bladder of the user/patient through the urethra. The member 12 (in accordance with various embodiments) can preferably contain a biocompatible lubricious and/or antimicrobial coating on at least an outer surface thereof. Suitable non-limiting examples of such lubricious and antimicrobial coatings are disclosed in U.S. Pat. Nos. 4,585,666; 5,558,900; 5,077,352; 5,179,174; 6,329,488 (suitable for, e.g., polysiloxane substrates); U.S. Pat. Nos.6,716,895; 6,949,598; 7,179,849, and, WO 2007/050685, each of which is incorporated by reference in its entirety.

The antimicrobial agent used on the catheter may be one listed in an over the counter (OTC) monograph. Biocompatible coatings conform with the following tests: mucosal irritation, sensitization, cytotoxicity, acute systemic toxicity, and implantation. ("Tripartite Biocompatibility Guidance for Medical Devices," DSMA (Apr. 24, 1987) (Updated May 21, 1996)). The purpose of the wetting fluid is to maintain hydration of the lubricious coating such that upon insertion of the conduit into a user, at least an outer portion thereof is extremely slippery, facilitating insertion.

The members 10, 12 may preferably be constructed from a suitable polymeric material, such as polyethylene or polypropylene. The components of the catheter disclosed herein can also be made from various well-known materials. For example, the portions of the assembly other than the member 12 can be made of polyvinyl propylene, polyvinyl chloride, polyethylene, and other types of suitable polymeric materials. The components can be molded or extruded according to well-known manufacturing techniques.

Materials commonly used to make the member 12 include, but are not limited to natural rubber latexes (available, for example, from Guthrie, Inc., Tucson, Ariz.; Firestone, Inc., Akron, Ohio; and Centrotrade USA, Virginia Beach, Va.), silicones (available, for example, from GE Silicones, Waterford, N.Y., Wacker Silicones, Adrian, Mich.; and Dow Corning, Inc., Midland, Mich.), polyvinyl chlorides (available, for example, from Kaneka Corp., Inc., New York, N.Y.), polyurethanes (available, for example, from Bayer, Inc., Toronto, Ontario, Rohm & Haas Company, Philadelphia, Pa.; and Ortec, Inc., Greenville, S.C.), plastisols (available, for example, from G S Industries, Bassett, Va.), polyvinyl acetate, (available, for example from Acetex Corp., Vancouver, British Columbia) and methacrylate copolymers (available, for example, from Heveatex, Inc., Fall River, Mass.). Natural rubber latexes, polyurethanes, and silicones are preferred materials. Any combination of the foregoing materials may also be used in making catheters. In one embodiment, a rubberize layer that includes latex and a methacrylate is used with build up and finish layers that include latex but not methacrylate. In another embodiment, a polyurethane rubberize layer is used with latex build up and finish layers. In another embodiment, a polyvinyl acetate and latex rubberize layer is used with latex build up and finish layers. Each of the foregoing embodiments in which specific Young's Modulus values are specified may be used with any material.

The urinary catheter, and in particular member 12, of the present invention can be manufactured by a variety of well-known methods. For example, according to various embodiments, the catheter is manufactured by dipping. An elongated rod or "form" is dipped into a first liquid coating material to form a layer of coating material on the form. The form has the shape and dimensions of the lumen of the catheter. This first coating layer forms the inner or rubberize layer of the catheter. Once the first layer has dried, the form is then dipped into a second coating material to build up an intermediate or build up layer. Multiple dips into the second coating material may be desirable to build up an intermediate layer of appropriate thickness. The build up layer is then dried. The finish layer is applied with a subsequent dip and is dried. The catheter may be stripped from the form, and eyelets may then be formed thereon. Further manufacturing steps may be found in U.S. Pat. No. 7,628,784, the disclosure of which is incorporated by reference herein.

The member 12 may preferably be in the range of about 8 cm to about 18 cm, and, it may have an elliptical cross-sectional shape similar to the shape of the male urethra. Different lengths, sizes (e.g., diameter, width, etc.), and configurations are possible for the catheter, depending on the user's anatomy. For female users, the insertable length may range from 40 to 100 mm, for example 50 to 80 mm, such as 55 to 75 mm. For male users, the insertable length can range from 170 to 260 mm, such as 190 to 240 mm, for example 230 mm. The tip design can vary according to the needs of a user, for example, the catheters disclosed herein can be provided with a coude tip. The catheter may have a round or substantially round cross-sectional shape, an oval cross-sectional shape, or any other cross-sectional shape that may facilitate insertion into the body of a user/patient, and in particular, into the bladder of the user/patient through the urethra. According to various embodiments, the shape of the catheter can also be variable along its length.

This invention has been described and specific examples of the invention have been portrayed. While the invention has been described in terms of particular variations and illustrative figures, those of ordinary skill in the art will recognize that the invention is not limited to the variations of figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claim:

1. A catheter comprising:
    an elongate member having a diameter extending between a proximal end and a distal end of the elongate member, the distal end having a pre-drainage opening;
    a plurality of drainage openings in a distal section of the elongate member proximal of the pre-drainage opening, the drainage openings comprising one of:
        two circumferentially spaced elongate openings;
        at least three staggered openings; and
        an array of staggered openings; and
    a sleeve member having an internal diameter between a proximal end and a distal end of the sleeve member that substantially matches the diameter of the elongate member and being arranged on the elongate member, such that, following insertion of at least the distal end of the elongate member and the distal end of the sleeve member through a urethra and into a bladder of a patient, the sleeve member is slidable between a first position in which the sleeve member covers the plurality of drainage openings inside the bladder and a second position which allows fluid to flow from the bladder through the drainage openings and into a lumen of the elongate member, wherein the second position of the sleeve member is proximal the first position of the sleeve member.

2. The catheter of claim 1, wherein the sleeve member comprises a proximal end that facilitates gripping by a user.

3. The catheter of claim 1, wherein the sleeve member comprises one of:
    a hydrateable coating arranged at least on an outer surface of a distal end of the sleeve member;
    a lubricious coating arranged at least on an outer surface of a distal end of the sleeve member; and
    a hydrophilic biocompatible coating arranged at least on an outer surface of a distal end of the sleeve member.

4. The catheter of claim 1, wherein each of the plurality of drainage openings is generally oval-shaped.

5. The catheter of claim 1, wherein the sleeve member further comprises a lubricious antimicrobial coating arranged at least on an outer surface of a distal end of the sleeve member.

6. The catheter of claim 1, further comprising a sealing member arranged to provide sealing between the sleeve member and the elongate member.

7. The catheter of claim 1, wherein the elongate member comprises one of:
    a hydrateable coating arranged at least on an outer surface of the distal end of the elongate member;
    a lubricious coating arranged at least on an outer surface of the distal end of the elongate member; and
    a hydrophilic biocompatible coating arranged at least on an outer surface of the distal end of the elongate member.

8. A method of draining a bladder using the catheter of claim 1, the method comprising:
    inserting at least the distal end of the elongate member and the distal end of the sleeve member through the urethra and into the bladder;
    confirming that the distal end of the elongate member is properly inserted into the bladder; and
    retracting the sleeve member from the first position to the second position to expose the plurality of drainage openings while the distal end of the elongate member is within the bladder such that fluid flows from the bladder through the plurality of drainage openings and into a lumen of the elongate member.

9. A method of draining a bladder using the catheter of claim 1, the method comprising:
    inserting a guide wire into the bladder;
    guiding the distal end of the elongate member into the bladder over the guide wire; and
    retracting the sleeve member to expose the plurality of drainage openings.

10. The catheter of claim 1, wherein the plurality of drainage openings are the two circumferentially spaced elongate openings.

11. The catheter of claim 1, wherein the plurality of drainage openings are the at least three staggered openings.

12. The catheter of claim 1, wherein the plurality of drainage openings are the array of staggered openings.

13. The catheter of claim 1, wherein the distal end of the elongate member remains straight when the sleeve member is in the second position.

14. The catheter of claim 1, wherein in the first position, the fluid is prevented from flowing through the plurality of drainage openings.

15. The method of claim 8, wherein all of the catheter that is inserted into the bladder consists of a portion of the elongate member and a portion of the sleeve member.

16. The catheter of claim 1, wherein a length from the proximal end to the distal end of the sleeve member and the internal diameter remain the same in the first position and the second position.

17. The catheter of claim 1, wherein the pre-drainage opening is in a tip at the distal end of the elongate member.

* * * * *